United States Patent [19]

van Oort et al.

[11] Patent Number: 5,720,769
[45] Date of Patent: Feb. 24, 1998

[54] SYSTEM AND METHOD FOR ADJUSTING SENSOR THRESHOLD IN A RATE RESPONSIVE PACEMAKER

[75] Inventors: Geeske van Oort, Nieuwleusen; Gustaaf A. P. Stoop, Dieren, both of Netherlands

[73] Assignee: Vitatron Medical, B.V., Dieren, Netherlands

[21] Appl. No.: 744,090

[22] Filed: Nov. 5, 1996

[51] Int. Cl.⁶ .................................................. A61N 1/00
[52] U.S. Cl. ............................................................. 607/17
[58] Field of Search .................................. 607/9, 17, 18, 607/19, 20, 21

[56] References Cited

U.S. PATENT DOCUMENTS

| | | |
|---|---|---|
| 5,065,759 | 11/1991 | Begemann et al. |
| 5,074,302 | 12/1991 | Poore et al. ............... 607/19 |
| 5,154,170 | 10/1992 | Bennett et al. |
| 5,226,413 | 7/1993 | Bennett et al. |

*Primary Examiner*—Scott M. Getzow
*Attorney, Agent, or Firm*—Woodcock Washburn Kurtz Mackiewicz & Norris LLP

[57] ABSTRACT

There is provided a rate responsive pacemaker system and method employing an activity-type sensor for deriving signals for determining pacing rate, wherein the activity sensor threshold is automatically adjusted as a function of monitored sensor output. In a preferred embodiment, activity counts are categorized on a histogram basis, and the histogram data is stored over a selected period of time. The activity data in histogram form is then analyzed and compared to predetermined criteria to determine whether threshold seems to be proper, or whether threshold adjustment is indicated. The adjustment algorithm provides different degrees of adjustment depending upon the circumstances. Specifically, where the data suggests too many or too few counts within an expected range, the threshold is adjusted as a function of whether the analyzed outputs are only a little bit out of the expected range or quite a bit out of the expected range. The algorithm also determines whether the sensor response accurately reflects patient rest. Another specific feature of the invention is determination of when the sensor is picking up false positives and thus improperly responding to extraneous signals such as patient's cardiac contractions.

14 Claims, 7 Drawing Sheets

SYSTEM AND METHOD FOR ADJUSTING SENSOR THRESHOLD IN A RATE RESPONSIVE PACEMAKER

FIELD OF THE INVENTION

This invention relates to rate responsive cardiac pacemakers and, more particularly, to adjustment of the sensor or sensors used for controlling pacing rate.

BACKGROUND OF THE INVENTION

Rate responsive cardiac pacemakers provide the benefit of varying pacing rate in accordance with patient cardiac demand. Thus, when the patient is active and the body calls for increased blood flow, the rate responsive (RR) pacemaker increases pacing rate, resulting in increased cardiac output. Similarly, at times of rest, either inactivity or sleep, the pacing rate is allowed to drop to a low rate, which has the dual benefit of corresponding to reduced patient demand and also saving pacemaker battery energy. Such RR pacing systems have become very popular, and are designated by the letter R, e.g., VVIR, DDDR, etc.

The reliability of a rate responsive pacemaker is understandably tied to the sensor, or sensors used to monitor one or more parameters indicative of desired pacing rate. The preferred sensor used in the pacemaker system and method of this invention is the activity sensor, which is a transducer that provides an output corresponding to body movement or activity, which output is transformed into an activity count which is representative of desired pacing rate. Reference is made to U.S. Pat. No. 5,065,759, issued to the assignee of this application and incorporated herein by reference, for a discussion of the relation of activity count to pacing rate. As used herein, ACT refers to the number of counts from the activity sensor during a unit of time, specifically 20 seconds. It is to be understood that, while the invention relates to a rate-responsive pacemaker having an activity sensor in its preferred embodiment, the invention covers pacemakers with an activity sensor and one or more other sensors, such as disclosed in the above-referenced patent, as well as rate responsive pacemakers with one or more similar types of sensors. As used herein, an activity-type sensor means a transducer and circuit which provides an output each time the transducer output rises above a predetermined level.

A problem that must be solved in a rate responsive pacemaker utilizing an activity-type sensor, is that of properly setting the sensor threshold, ACT_Th, for producing a count. The transducer delivers an analog signal that rises in amplitude and/or frequency in response to body movement, and when the signal exceeds ACT-Th, a count is produced. The problem is to set or program a threshold that is optimum for the pacemaker and patient involved, i.e., one which is sensitive enough to properly detect body movement, but which is sufficiently insensitive so that it does not sense small extraneous movements such as due to the patient's own heart contraction, or respiration. While often the threshold can be set at a median, or nominal acceptable level at the time of implant, circumstances may change which indicate a change in ACT_Th. For some patients, depending on weight or implant method (sub or supra-muscular), the initial setting might not be optimal. It is noted that for some rate response pacemakers, automatic correlation optimization may correct for an incorrect sensor setting. However, for sensors such as activity, if threshold is incorrectly set, the response can be simply on or off, and the correlation algorithm cannot provide correction. Further, there is a chance that the pocket characteristics may change in time, particularly after implant, by healing of the pocket and further by change in weight, or a change in life style or fitness level. Note also that it is desired to provide automatic adjustment to save the physician programming valuable time. We have made studies of patients with implanted pacemakers where data was recorded at different activity threshold settings. We obtained activity histograms, wherein ACT counts were obtained for "bins" representing counts per 20 seconds over 0–10, 10–20, 20–30, etc.; as well as 0–5 and 5–10. The results indicate that while the influence of the activity threshold is usually relatively small at higher levels of exercise, there clearly are conditions where it may be desirable to automatically adjust ACT_Th. Our investigations have shown that for a typical activity sensor, a proper threshold results in an activity count of 0–10 counts in a 20 second interval for 60–80% of such intervals. In other words, if the threshold is properly set, during 60–80% of continuously monitored 20 second intervals, the activity count (ACT) should be in the range of 0–10 counts. Using this criteria, if the percentage of ACT counts falls either or above this range, an adjustment in threshold is indicated. Further, we have analyzed data to indicate what the count should be when a patient is at rest, i.e., not active. This data suggests that when at rest, ACT should be found between 0 and 5on more occasions than between 5 and 10. From this histogram data, we have made the following conclusions: in all patient histograms, the percentage of events in the first bin (0–10) is lower for a lower ACT_Th compared to a higher ACT_Th. This means that when threshold is programmed higher, less counts are sensed, so more events fall into the lowest bin. It is also seen that in comparing equal bins, the counts decrease from the lowest bin to the highest bin, except for the circumstance where the sensor is providing false positives due to the patient heart contractions. We also correlated data comparing monitored patient rest time with histogram data, and determined that the percentage of rest can be defined as the percentage of time where the number of activity counts is less than 5 counts/20 sec. Even when the patient is presumed to be sitting quietly, there may be extra events that are counted, but an ACT of 5 appears to be an accurate break point between rest and activity, even though absolute rest can better be indicated as less than 2 counts/20 sec. This data also reflects that when cardiac contractions are detected by the activity sensor, i.e., false positives, a relatively large peak can be seen in a bin around the heart frequency, i.e., 20–40 counts/20 sec.

SUMMARY OF THE INVENTION

We have determined that in many patients there is a need in a rate responsive pacemaker for monitoring sensor response or output over a period of time, processing the output data and determining whether an adjustment of threshold is needed or desirable. It is accordingly an object of this invention to provide a rate responsive pacemaker having at least one sensor responsive to patient activity for deriving a signal indicative of desired pacing rate, the sensor output feeding a circuit for providing an activity output whenever the sensor signal exceeds a given threshold, and for providing automatic adjustment of the activity sensor threshold when conditions indicate that an adjustment would provide an improved indication of desired pacing rate.

In accordance with the above object, there is provided a rate responsive pacemaker having at least an activity-type sensor which produces a signal corresponding to patient activity, and processing circuitry for processing the signal to provide an indication of desired pacing rate. In a preferred embodiment, the processing circuitry provides an output count whenever the sensor exceeds a given threshold, and a determination is made of the rate of counts, from which the desired pacing rate is determined. In the pacemaker and method of this invention, the activity counts are processed over a predetermined adjustment period, e.g., a week, and analyzed to provide an activity count profile, or history. For example, in a preferred embodiment, a count histogram is accumulated with the counts in different histogram bins representing the number of counts per a given increment of time which had occurred within respective different count ranges. From this histogram data a determination is made as to whether the activity threshold should be adjusted, and if so, in what direction and by how much. The determination is made by comparing the accumulated histogram data to predetermined criteria to see whether the activity count data has a profile within expected ranges. The invention further provides for checking accumulated data to see whether there is an indication of false positives due to counting patient heart contractions as activity.

DETAILED DESCRIPTION OF THE PREFERRED EMBODIMENTS

Figure 1:
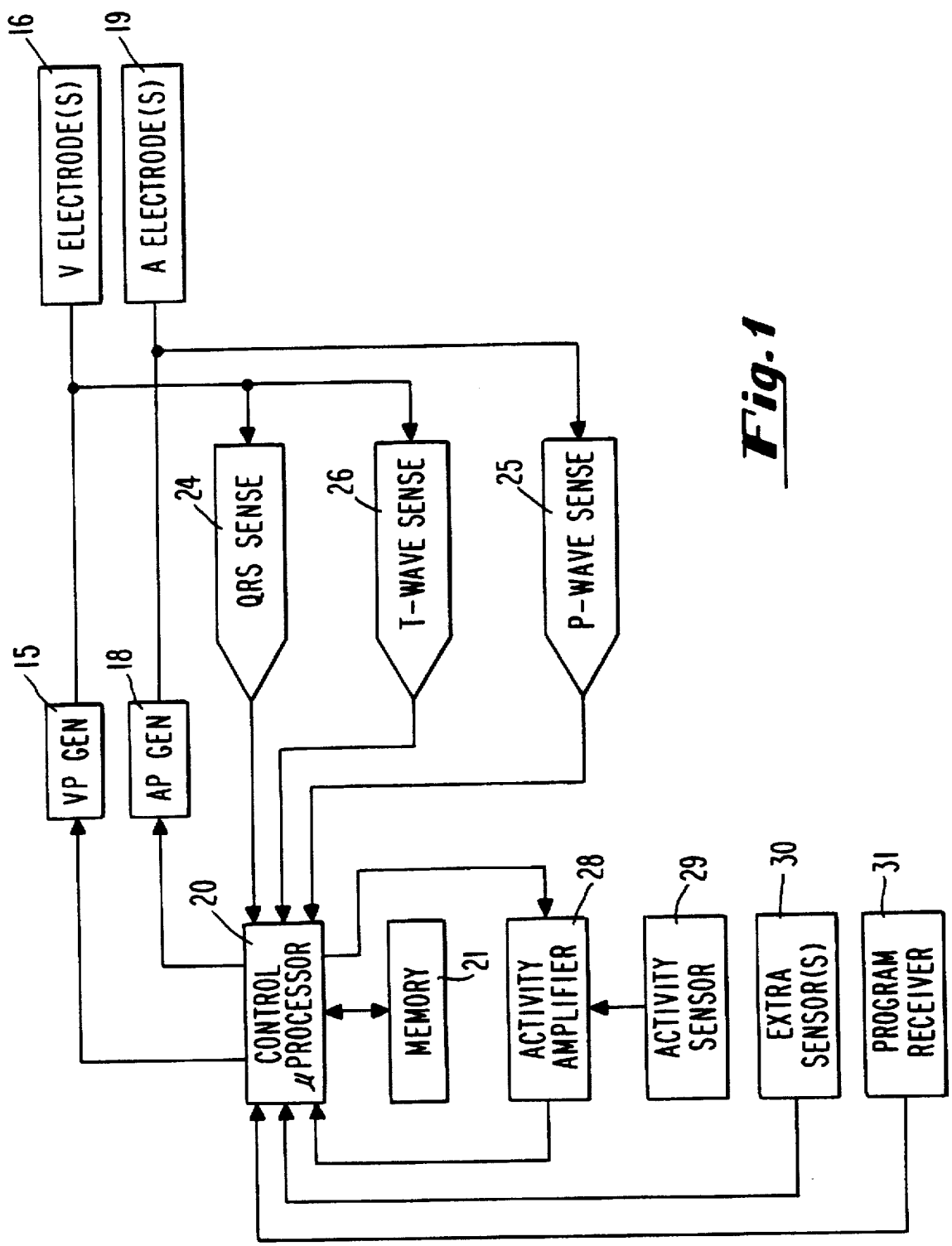
FIG. 1 is a block diagram illustrating the basic circuit components of a pacemaker in accordance with this invention.

Referring now to FIG. 1, there are illustrated the primary components of a pacemaker in accordance with this invention, including an activity sensor and an activity amplifier for providing activity counts. The pacemaker is illustrated as a dual chamber pacemaker, but it is to be understood that the system and method of this invention are applicable to a single chamber, dual chamber, or indeed multiple chamber pacemaker. A ventricular pace generator 15 is illustrated as providing pacing pulses to one or more ventricular electrodes illustrated at 16. Likewise, an atrial pulse generator 18 provides pacing pulses to one or more atrial electrodes illustrated at 19. The timing and characteristics of the delivered ventricular and/or atrial pace pulses are controlled by control block 20, which suitably includes a microprocessor in a well-known fashion. The microprocessor interconnects with memory 21. It is, of course, understood that the invention may be carried out with any suitable arrangement of software and hardware circuits, although software control is presently preferred for carrying out many functions. Sense signals at the ventricular and atrial electrodes are transmitted to QRS sense circuit 24 and P-wave sense circuit 25, respectively, the outputs of which are connected through to control block 20 for controlling timing of the pacemaker, in a known manner.

Focusing on the specific purpose of the invention, an activity sensor 29 is illustrated, which suitably is a transducer that responds to motion and provides an analog output which is inputted to activity amplifier 28. Amplifier 28 has an adjustable threshold which is controlled by control block 20, as indicated. Whenever the output of the sensor 29 exceeds the threshold value, the activity amplifier provides a pulse output which is delivered to control block 20, for processing and control purposes. As discussed above, the threshold is suitably set so that any signal excursions from the sensor which are truly reflective of activity produce a pulse output, hereinafter referred to as a count; while at the same time the threshold is high enough that the pacemaker is insensitive to noise and random signals which are not reflective of patient activity, e.g., respiration, cardiac contraction, and other extraneous events. Circuits for providing adjustment of thresholds are well known in the art, and many present day pacemakers provide for programmability of amplifier thresholds.

Still referring to FIG. 1, at block 30 there is also illustrated an extra sensor or sensors, which provide rate-indicating inputs to control block 20. For example, as discussed in the above-referenced U.S. Pat. No. 5,065,759, a pacemaker may utilize an activity sensor together with a second sensor, obtaining information from each of the two or more sensors. In the referenced of U.S. Pat. No. 5,065,759, QT interval is a second ram-indicating parameter, in which case a T-sense amplifier is also provided, as illustrated at 26. Thus, the invention specifically contemplates application to a dual or multiple sensor rate responsive pacemaker, where one or more of the sensors is of the type that generates an output pulse, or count, when the sensor signal exceeds a predetermined threshold. Also shown at block 31 is a programmer receiver for receiving data from an external programmer and connecting it through to the control block 20, in a known manner.

Figure 2:
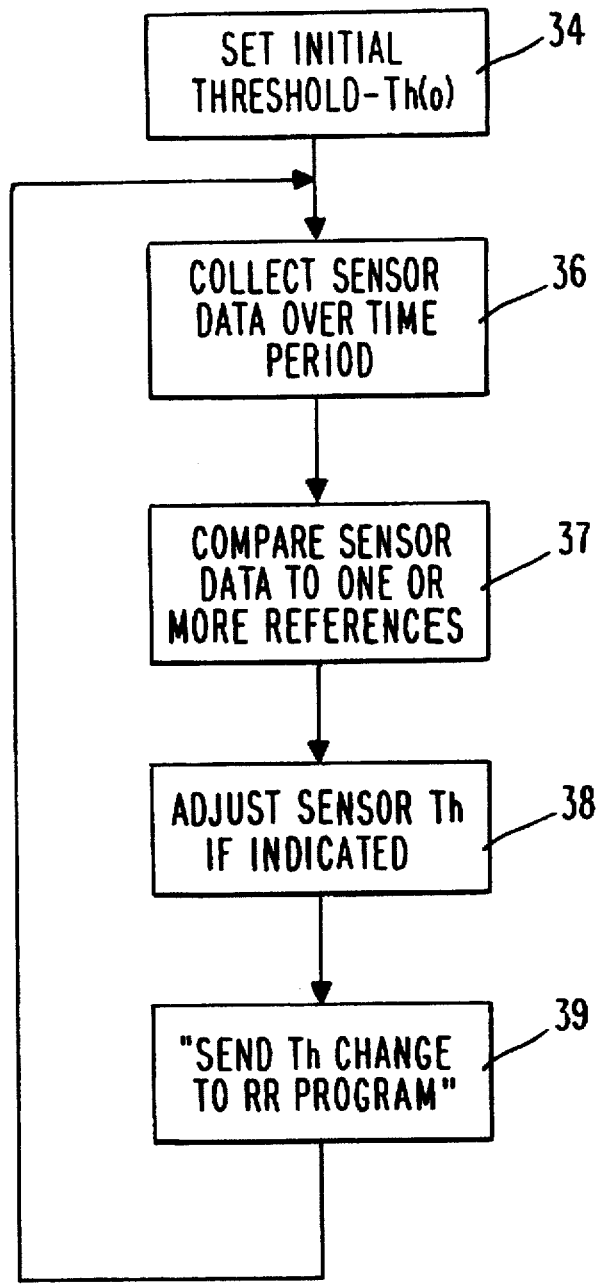
FIG. 2 is a brief flow diagram showing the primary steps of the process of this invention.

Referring now to FIG. 2, the primary steps of the process and implementation of this invention are shown. At block 34, the initial threshold ($Th_o$) is set. The pacemaker is initially set at the factory; it may be set to a default setting when switching the Activity sensor on, or may be set by the physician at another setting. Following implant, it is necessary to let conditions stabilize, since ACT threshold should be set only after initial variations caused by healing of the pocket and recovering of the patient after implant have faded. After this, sensor data is collected over a period of time, e.g., two weeks, as represented at block 36. After expiration of the collection time period, the sensor data is processed and compared to one or more references to determine whether it is suitable. Thus, in a general sense the pacemaker looks to determine whether the data appears to reflect excessive activity counts, which would represent too low a threshold, or does not reflect sufficient activity counts for a patient known to have exercised, which would reflect too high a threshold. Following the comparison and analysis of the sensor data at 37, at step 38 the sensor threshold is adjusted, assuming that the data indicates that an adjustment is desired. Of course, if the sensor data appears to be nominal and within predetermined criteria, then no adjustment is made. Following this, at step 39 the change in threshold is sent to the rate response program for adjustment of that program if required. As a general proposition a change in sensor threshold may or may not result in a need to change the correlation algorithm, depending upon the nature of the sensor output and also the correlation algorithm itself. Following this, the process loops back to step 36 and again starts to collect sensor data over a predetermined time period, which time period itself can be adjusted based upon the pacemaker history.

Figure 3:
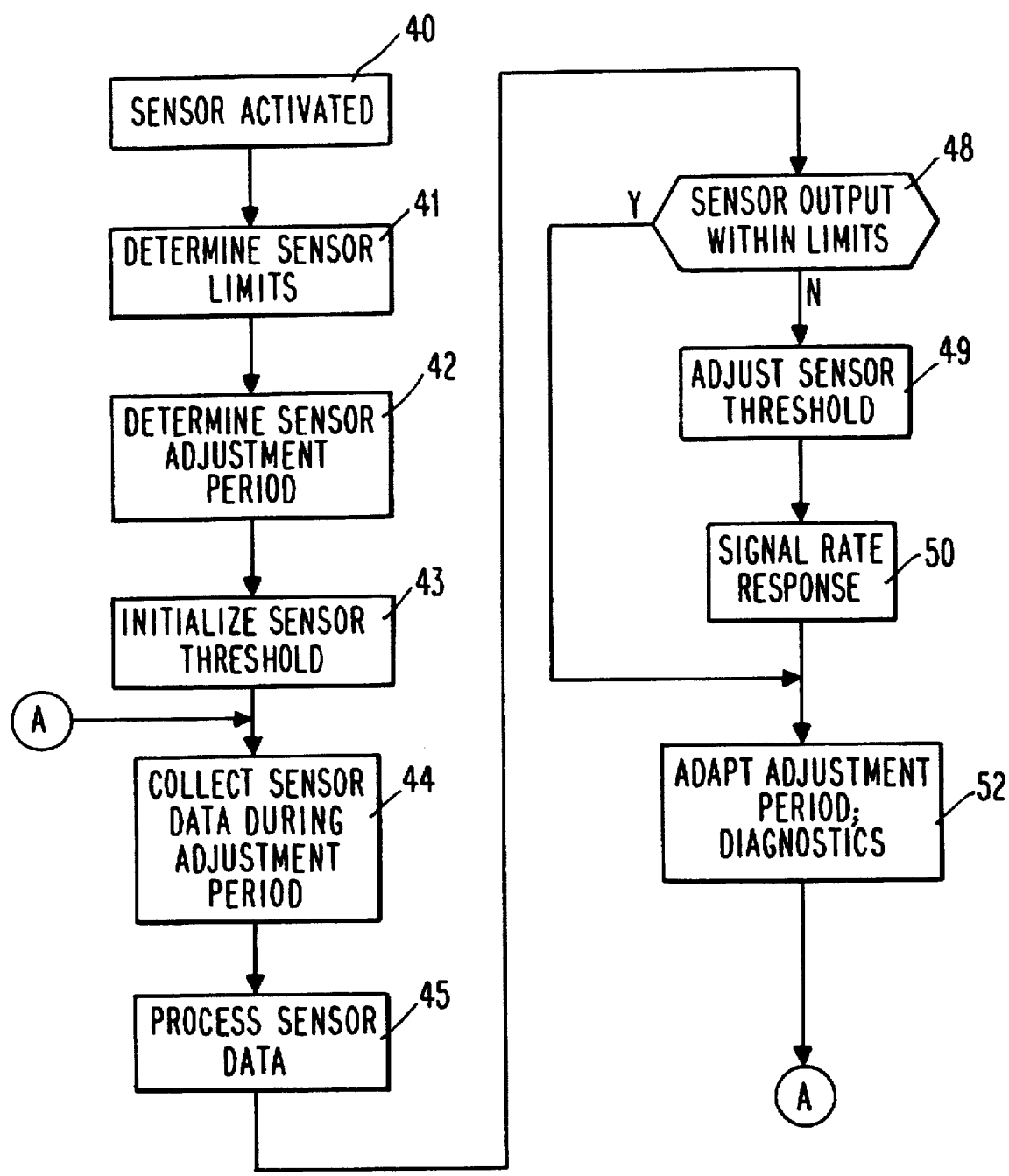
FIG. 3 is a flow diagram that is a more derailed flow diagram of the steps taken in collecting sensor data over a period of time and determining whether sensor threshold should be adjusted.

Referring now to FIG. 3, there is shown a somewhat more detailed flow diagram of steps taken in gathering data with which to analyze sensor threshold, and subsequent adjustment of sensor threshold where indicated. Upon pacemaker implant, the sensor is activated, as indicated at block 40. The pacemaker also sets sensor limits, or criteria for determining whether the sensor threshold is properly set. These sensor limits or criteria are suitably programmed at the time of implant. For example, as discussed above, the bin limits for collecting data in histogram bins, as well as decision percentages, are entered into memory for use in processing of the collected data. Following this, as indicated at 42, a sensor adjustment period is determined and stored in the pacemaker. The initial adjustment period may be relatively short, in the range of about one week, although subsequently greater time periods may be adapted on the assumption that conditions have stabilized and less frequent examination is required. After this, at 43, the sensor threshold is initialized, usually by programming a nominal mid-range value.

Continuing with the flow diagram of FIG. 3, at 44 the pacemaker collects sensor data during the adjustment period. In the preferred illustration of this invention, activity counts are collected over a 20 second interval to provide an ACT value, which is then stored in an appropriate bin, e.g., less than 10, 10–20, etc. The ACT counter is then cleared and the next 20 second count is obtained, this being repeated throughout the predetermined adjustment period. After termination of the adjustment period, the sensor data is processed as indicated at block 45. Such processing may, for example, include comparing counts in each histogram bin and determining whether the count in one or more bins reflects a percentage of all counts that is within a prescribed range. After this processing, at 48 it is determined whether the sensor output is within the predetermined limits, or criteria. In the preferred example of this invention, this involves determining whether the bin representing ACT $\leq 10$ constitutes between 60 and 80% of all counts. It is to be noted that any criteria may be established, simple or complex, for making an evaluation as to whether the sensor output is acceptable and within limits. At step 49, the sensor threshold is adjusted, if at step 48 the data is determined to be not within limits. After this, the pacemaker signals the rate response algorithm that an adjustment has been made, i.e., the information concerning the threshold adjustment is given to the rate response algorithm for an adjustment algorithm if necessary. At 50, the change in threshold is transferred to the RR routine, for possible use in adjusting the RR correlation algorithm. Returning to 48, if it is found that the sensor output meets the inputted criteria, then steps 49 and 50 are bypassed. Finally, at 52, the pacemaker determines whether to adapt the adjustment period, i.e., lengthen it, and also carries out any indicated diagnostics. It is noted that with time, and also considering whether there have been any earlier cases where a threshold adjustment has been found to be necessary, the adjustment period can be lengthened. A change in the adjustment period can be made automatically or by physician programming. Likewise, all or any selected portion of the sensor data can be stored for diagnostic evaluation, e.g., in combination with other stored data representative of patient conditions and events. After this, the program exits as indicated at A, resets all bin counters, and starts the collection process again at block 44.

Figure 4:
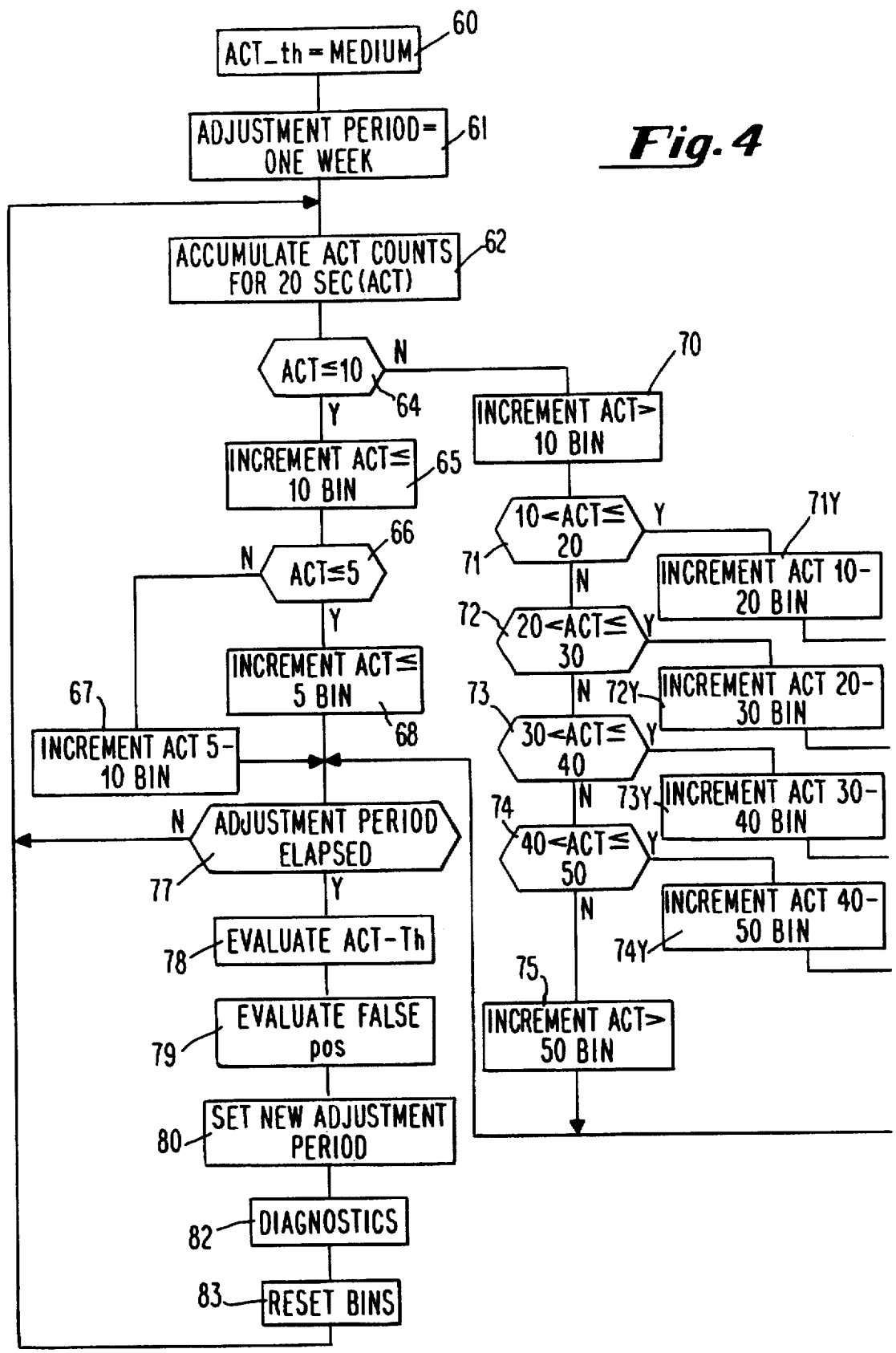
FIG. 4 is a derailed flow diagram showing specific steps for accumulating a count histogram for use in adjustment of an activity sensor threshold, in accordance with this invention.

Referring now to FIG. 4, there is shown a more detailed flow diagram for collecting ACT histogram data. At 60, the activity threshold is initially set to a medium setting. At 61, the adjustment period is initially set to one week. At 62, the pacemaker accumulates the activity counts for 20 seconds and provides an ACT output. At 64, it is determined whether ACT is $\leq 10$. If yes, the ACT $\leq 10$ is incremented at 65. Then, at 66, it is determined whether ACT is $\leq 5$. This is done in order to provide data for determining whether the activity sensor is providing a proper output when the patient is at rest, as is discussed in more detail below. If ACT is $\leq 5$, the appropriate bin is incremented at 68. If ACT is not $\leq 5$, the 5–10 bin is incremented as shown at 67. Returning to (64, if ACT is >10, then the algorithm branches to block 70 and increments the ACT >10 bin. At 71, it is determined whether $10<ACT \leq 20$. If yes, the 10–20 bin is incremented at 71Y, and if no, at 72 it is determined whether $20 \leq ACT \leq 30$. If yes, the 20–30 bin is incremented at 72Y, and if no, at 73 it is determined whether $30 \leq 40$. If yes, the 30–40 bin is incremented at 73Y, and if no, at 74 it is determined whether whether $40 \leq 50$. If yes, the 40–50 bin is incremented at 74Y, and if no, at 75 the >50bin is incremented. Following incrementing of the appropriate bin, the routine proceeds to block 77 and determines whether the adjustment period has elapsed. If no, the routine branches back to 62 and loops through again to process the next value of ACT. If yes, the routine goes to block 78 and evaluates the data, adjusting ACT_Th where indicated. The illustration of the steps involved in adjustment of ACT_Th is provided in FIG. 5. Following this, the routine goes to block 79 and evaluates the data for false positives, and follow-up when indicated. A specific illustration of the steps corresponding to block 79 is set forth in FIGS. 6A and 6B. At block 80, the pacemaker determines whether a new adjustment period is appropriate, and sets same. At block 82, data is stored in relation to the diagnostics program. Following this, the histogram bins, or counters, are reset to 0 at 83, and the routine branches back to start all over again at block 62.

Figure 5:
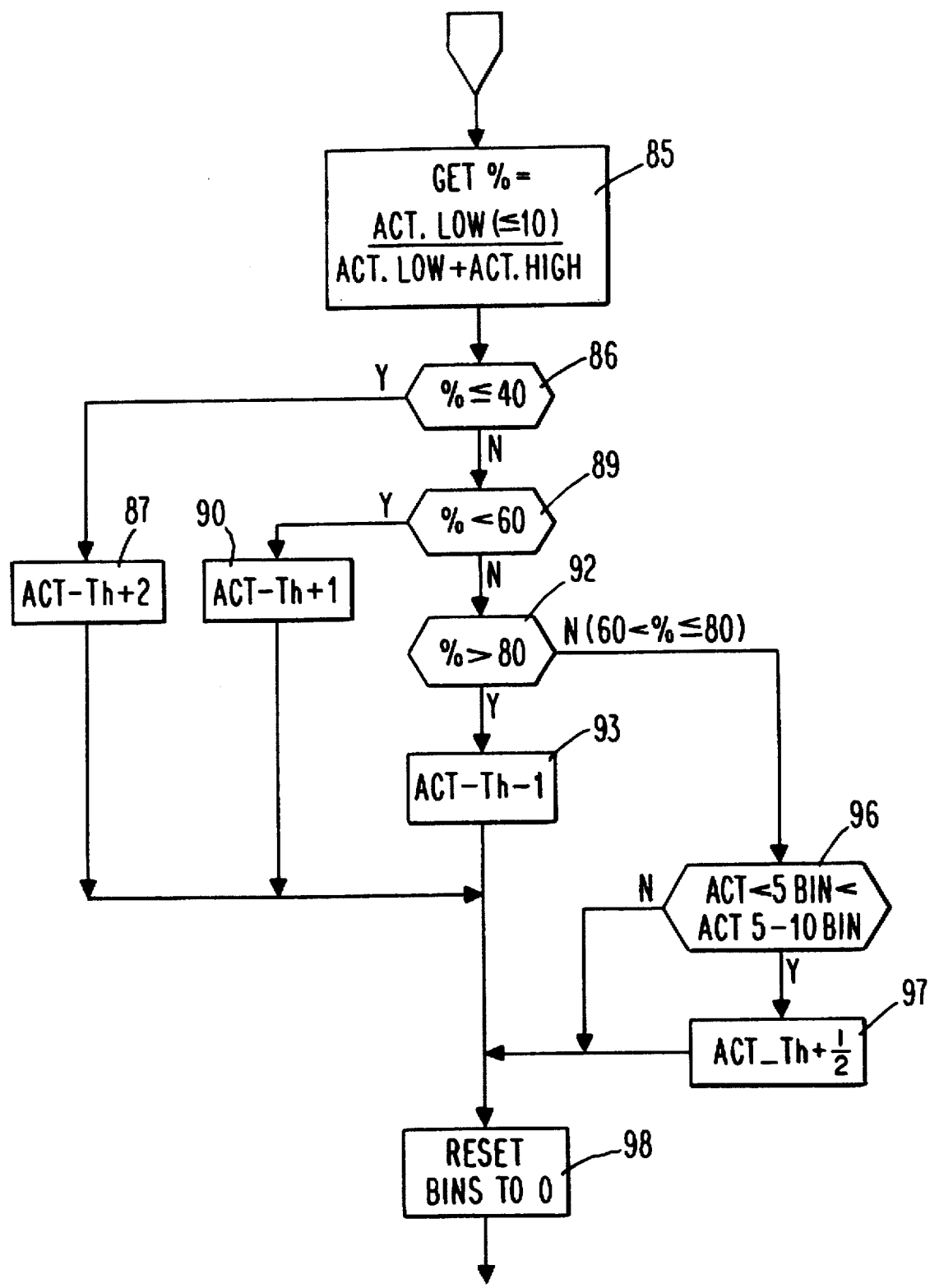
FIG. 5 is a derailed flow diagram of the steps taken in evaluating activity count data and adjusting activity threshold when indicated.

Referring now to FIG. 5, there is shown an illustration of the preferred embodiment for determining when the ACT histogram data indicates that there should or should not be an adjustment of ACT_Th. AT 85, the pacemaker gets a percentage defined as the ratio of ACT.low to ACT.low+ACT.high, where ACT.low is the value of the $\leq 10$ bin, and ACT.high is all counts over 10. As discussed above, the premise here is that evaluation of the efficacy of the threshold setting can be made by determining whether the percentage of low counts compared to all counts is within the range of 60–80%. At 86, the percentage is tested to determine whether it is less than 40. If yes, this indicates that threshold is much too low and the routine branches to block 87 and increments ACT_Th by 2units. If no, the routine goes to 89 and determines whether % is less than 60. If yes, this means that it is between 40 and 60, threshold is moderately low, and the routine branches to block 90 and increments ACT_Th by 1. If the answer at 89 is no, the routine goes to 92 and determines whether % is greater than 80. If yes, meaning that the percentage is outside of the established desired range and threshold is too high, the routine goes to block 93 and decrements ACT_Th by 1. If the answer at 92 is no, meaning that the Activity.low percentage is within the desired 60–80% range, the routine branches to block 96 and compares the <5 and 5–10 bins. As discussed above, this comparison enables a determination of whether ACT counts while the patient is at rest are where they should be. Thus, over a period of a week or more, more than half of the low counts should be in the <5 bin, based on the premise that the patient is at rest more than in an active state. If more than half of the low counts are in the <5 bin, the routine branches to block 98. However, if the 5–10 bin contains more than half the counts, this indicates that some adjustment should be made, and the routine goes to block 97 and increments ACT_Th by one-half unit. At 98 the bins are reset to 0, and the routine exits.

Figure 6A:
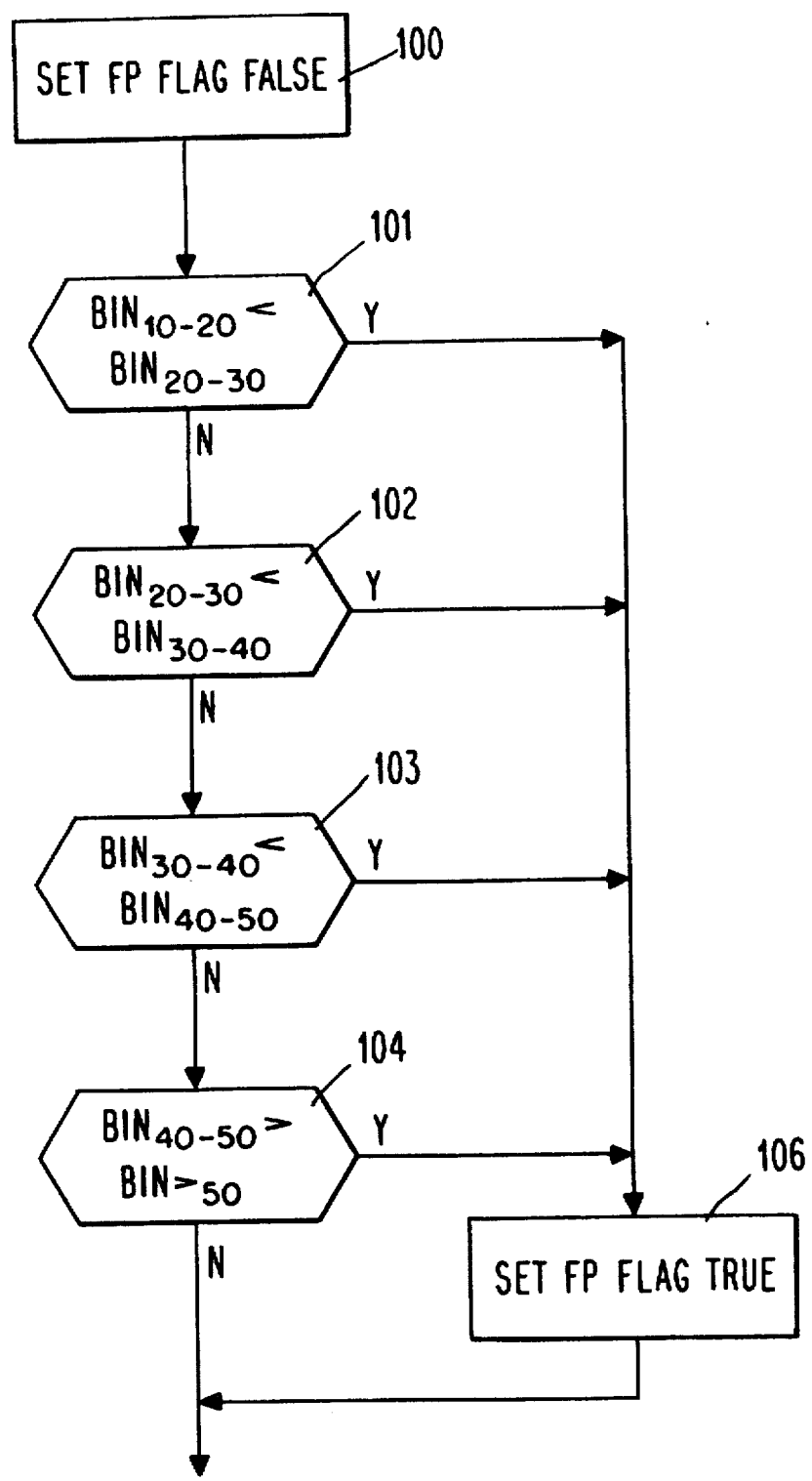
FIG. 6A is a flow diagram illustrating the steps taken to determine whether it is likely that the pacemaker activity counts contain false positives, i.e., whether activity counts reflect patient cardiac contractions as opposed to actual exercise.

Referring now to FIG. 6A, there is shown a routine for making a determination whether it is likely that false positives have been counted, i.e., there are counts that reflect sensor pick-up of heart contractions. As set forth above, in normal situations without false positives, each successively higher bin should contain fewer counts, meaning that there should be more counts in each bin than there are in the next higher bin. What has been found in cases where an activity sensor is picking up heart contractions is that there are an unexpected and excessive number of counts in the range of 20–40, which reflects a heart rate of 60–120. The routine of FIG. 6A checks for false positives by determining whether any bin contains fewer counts than the next higher bin. First, at 100, the FP flag is set to false. At 101, it is determined whether the bin which has accumulated ACT in the range of 10–20 has a count less than bin for 20–30. If yes, this indicates an anomaly, and the routine branches to block 106 and sets the FP flag true. If no, the routine branches to 102, then to 103, and then to 104, and in each instance makes the corresponding test. If in any case a bin is found to have accumulated fewer counts than the next higher bin, then the routine branches to block 106 and sets the flag true. If not, the routine exists.

Figure 6B:
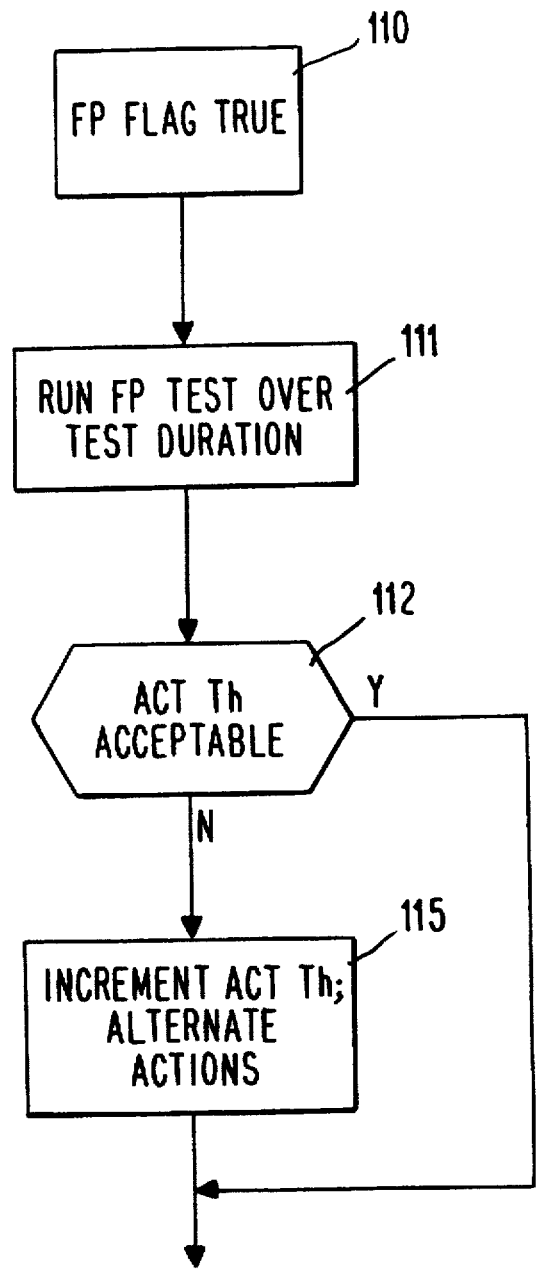
FIG. 6B is a flow diagram illustrating steps taken in response to an indication of false positives from the activity sensor.

Referring now to FIG. 6B, there is shown a brief flow diagram for responding to the situation where the FP flag is set true, which indicates likely false positives due to detecting patient heart beats. When this happens, the pacemaker can run an FP test over a predetermined test duration, as indicated at block 111. Such test is suitably done by programming rate changes, overdriving the heart with varying rates, and seeing if activity counts corresponding to the pacing rate are detected. Thus, if the rate is driven up to 120 for a predetermined interval, the pacemaker would look for ACT values in the range of 40 (since ACT, corresponds to 20 second intervals). Another manner of carrying out the test, where a dual sensor pacemaker having both ACT and QT is available, is to compare variations of ACT and QT over a period of time, and to analyze the comparison. If ACT does not follow QT to within given criteria, it can be concluded that ACT_Th is influenced by false positives. Following the running of the test at 111, at 112 it is determined whether the activity threshold is acceptable, or whether there are indeed too many false positives being detected. If the answer is that ACT_Th is not acceptable, then at 115 one or more steps can be taken. A relatively simple step is to increment ACT_Th, and examine the results over a period of time to see whether the decrease in sensitivity solves the problem. Alternate solutions include subtracting a predetermined number of counts corresponding to the heart beat; and blocking the activity sensor during a time window around the instant of each evoked response, and correcting for some real activity counts that would be blanked in such an event.

There has thus been described a system and method for automatically adjusting the threshold of an activity-type sensor which is in a rate responsive pacemaker, so as to optimize the sensor circuit output. The threshold adjustment enables continued accurate correlation between real patient activity and pacing rate. The invention also provides for the determination of false positives due to sensing extraneous conditions such as cardiac contractions, and adjusting threshold when such false positives are found.

We claim:

1. A rate responsive cardiac pacemaker, comprising:
a pace pulse generator for generating cardiac pace pulses, and rate control means for controlling the rate of generation of said pace pulses, said rate control means having
a sensor responsive to a predetermined patient parameter for continuously providing a sensor output signal having a varying signal level,
processing means for processing said sensor output signal to provide a count signal for use in controlling said rate whenever said sensor output signal meets predetermined sensor output signal level criteria,
accumulating means for accumulating data representative of said count signals over respective predetermined periods of time, and adjusting means for adjusting said criteria as a function of said data.

2. The pacemaker as described in claim 1, wherein said patient parameter is patient activity, and said criteria is sensor output signal amplitude threshold.

3. The pacemaker as described in claim 2, comprising analyzing means enabled after a predetermined period of time for analyzing said accumulated data with respect to predetermined count signal rate criteria, and said adjusting means has means for adjusting said sensor threshold as a function of whether said count signal rate criteria are met.

4. The pacemaker as described in claim 3, wherein said analyzing means comprises histogram means for accumulating histogram data representative of activity counts per unit of time.

5. A rate responsive cardiac pacemaker having a controllable pulse generator for generating pacing pulses at a controllable rate, and rate control means responsive to patient activity for controlling said rate, said rate control means comprising
activity sensor means for continuously providing an activity signal representative of patient activity and having a varying amplitude, and for producing an output count signal whenever said activity signal exceeds a predetermined amplitude threshold,
rate means for generating a rate control signal as a function of produced count signals,
data means for accumulating data reflective of the history of said output count signals, and
adjusting means for adjusting said amplitude threshold as a function of said accumulated history.

6. The pacemaker as described in claim 5, wherein said data means accumulates ACT counts which represent count signals per predetermined increment of time.

7. The pacemaker as described in claim 6, wherein said data means comprises histogram means for classifying and accumulating said ACT counts in predetermined histogram bins, and said adjusting means has comparing means for comparing accumulated bin counts over a given adjustment period and then comparing said accumulated bin counts to predetermined decision criteria.

8. The pacemaker as describe in claim 5, wherein said adjustment means comprises rest means for determining whether said accumulated data indicates that said threshold is properly set to produce reliable count signals during patient rest.

9. The pacemaker as described in claim 5, wherein said rate responsive means comprises an activity sensor circuit with an activity threshold, and said adjustment means comprises FP means for determining whether said accumulated data indicates that said threshold should be adjusted to prevent false positive counts.

10. A rate responsive pacemaker having a pace pulse generator for generating pace pulses, rate responsive means for deriving activity signals representative of patient activity and for developing rate control signals as function of said activity signals, rate means for classifying the rate of said activity signals over each of a plurality of successive time intervals, and means for detecting the occurrence of false positive activity signals as a function of said classifying.

11. The pacemaker as described in claim 10, wherein said rate responsive means comprises activity threshold means for obtaining a sensor signal representative of patient activity and deriving a said activity signal whenever said sensor signal has an amplitude above a predetermined threshold, and comprising adjustment means for adjusting said threshold when said classifying indicates that said threshold should be adjusted.

12. A method for automatically adjusting the threshold of an activity-type sensor circuit in a pacemaker implanted in a patient comprising detecting outputs from said sensor circuit over a predetermined adjustment time period;

classifying said outputs with respect to predetermined classification criteria;

analyzing said classified outputs with respect to predetermined decision data; and adjusting said threshold as a function of said analyzing.

13. The method as described in claim 12, comprising determining from said classified outputs when it is indicated that said sensor circuit is producing false positive outputs.

14. The method as described in claim 12, wherein said adjusting comprises determining whether said threshold is set for reliable indication when said patient is at rest.

* * * * *